United States Patent [19]
Granberg et al.

[11] Patent Number: 5,844,111
[45] Date of Patent: Dec. 1, 1998

[54] METHOD FOR PURIFYING AN INERT GAS WHILE PREPARING LOWER ALKYL ESTERS

[75] Inventors: Eric Paul Granberg; Richard Gerard Schafermeyer, both of Cincinnati; James Anthony Letton, Forest Park, all of Ohio

[73] Assignee: The Procter & Gamble Company, Cincinnati, Ohio

[21] Appl. No.: 486,847

[22] Filed: Jun. 7, 1995

[51] Int. Cl.$^6$ ........................................ C11B 3/00
[52] U.S. Cl. ................ 554/184; 554/169; 554/204; 554/206; 554/212; 95/291; 422/188; 422/193; 203/60
[58] Field of Search .................. 554/169; 95/157, 95/291; 534/184, 206, 204, 212; 422/188, 193; 203/60

[56] References Cited

U.S. PATENT DOCUMENTS

| | | | |
|---|---|---|---|
| 3,496,159 | 2/1970 | Spence | 260/97.6 |
| 4,431,838 | 2/1984 | Feldman et al. | 560/234 |
| 4,435,595 | 3/1984 | Agreda et al. | 560/234 |
| 4,668,439 | 5/1987 | Billersteen et al. | 554/167 |
| 4,847,430 | 7/1989 | Quang et al. | 568/697 |
| 4,895,971 | 1/1990 | Su | 558/346 |
| 4,976,892 | 12/1990 | Jeromin et al. | 260/410.7 |
| 5,254,722 | 10/1993 | Peukert et al. | 554/227 |

FOREIGN PATENT DOCUMENTS

| | | | |
|---|---|---|---|
| 564590 | 10/1958 | Canada | 554/169 |
| 2503195 | 7/1976 | Germany . | |
| 2109265 | 6/1983 | United Kingdom | B01J 10/00 |

OTHER PUBLICATIONS

U. R. Kreutzer, *Manufacture of Fatty Alcohols Based on Natural Fats and Oils,* JAOCS, vol. 61, No. 2 (Feb. 1984) pp. 343–348.

Kirk Othmer, Encyclopedia of Chemical Technology, vol. 9, 755–781 (4th Ed., 1994).

Kirk Othmer, Encyclopedia of Chemial Technology, vol. 1, pp. 878–885 (4th Ed., 1994).

G. Astarita et al., *Gas Absorption and Desorption with Reversible Instantaneous Chemical Reaction,* Chemical Engineering Science vol. 35, pp. 1755–1764.

G. Astarita, List of Publications, Chem. Eng. Sci., vol. 49, No. 5, pp. 575–580. (1994).

*Gas Absorption and Desorption with Reversible Instantaneous Chemical Reaction,* Chemical Engineering Science, vol. 47, No. 8, pp. 2125–2127 (1992).

P. V. Danckwerts et al., *The Absorption of Carbon Dioxide into Solutions of Alkalis and Amines,* Chemical Engineer, Review Series No. 2, (Oct., 1966).

Yu et al., *Design of Packed Towers for Selective Chemical Absorption,* Chemical Engineering Science, vol. 42, No. 3, pp. 425–433 (1987).

H. Sawistowski et al., *Performance of Esterification in a Reaction–Distillation Column,* Chemical Engineering Science, vol. 43, no. 2, pp. 355–360 (1988).

U.S. application No. 08/481,779, E. P. Granberg, filed Jun. 7, 1995.

*Primary Examiner*—José G. Dees
*Assistant Examiner*—Deborah D. Carr
*Attorney, Agent, or Firm*—Rose Ann Dabek; Daniel F. Nesbit; Jacobus C. Rasser

[57] ABSTRACT

A process for purifying an inert gas stream from a transesterification reaction wherein a lower alkyl alcohol is released during the reaction is claimed. A second use of the process is to make a lower alkyl, e.g., methyl, esters of fatty acids through a transesterification reaction using gaseous alcohols as a source of the lower alkyl alcohols. The alcohol is diluted with nitrogen or other inert gas carrier and reacted with a fatty acid ester, preferably a triglyceride, to form the corresponding methyl or lower alkyl fatty acid ester.

31 Claims, 1 Drawing Sheet

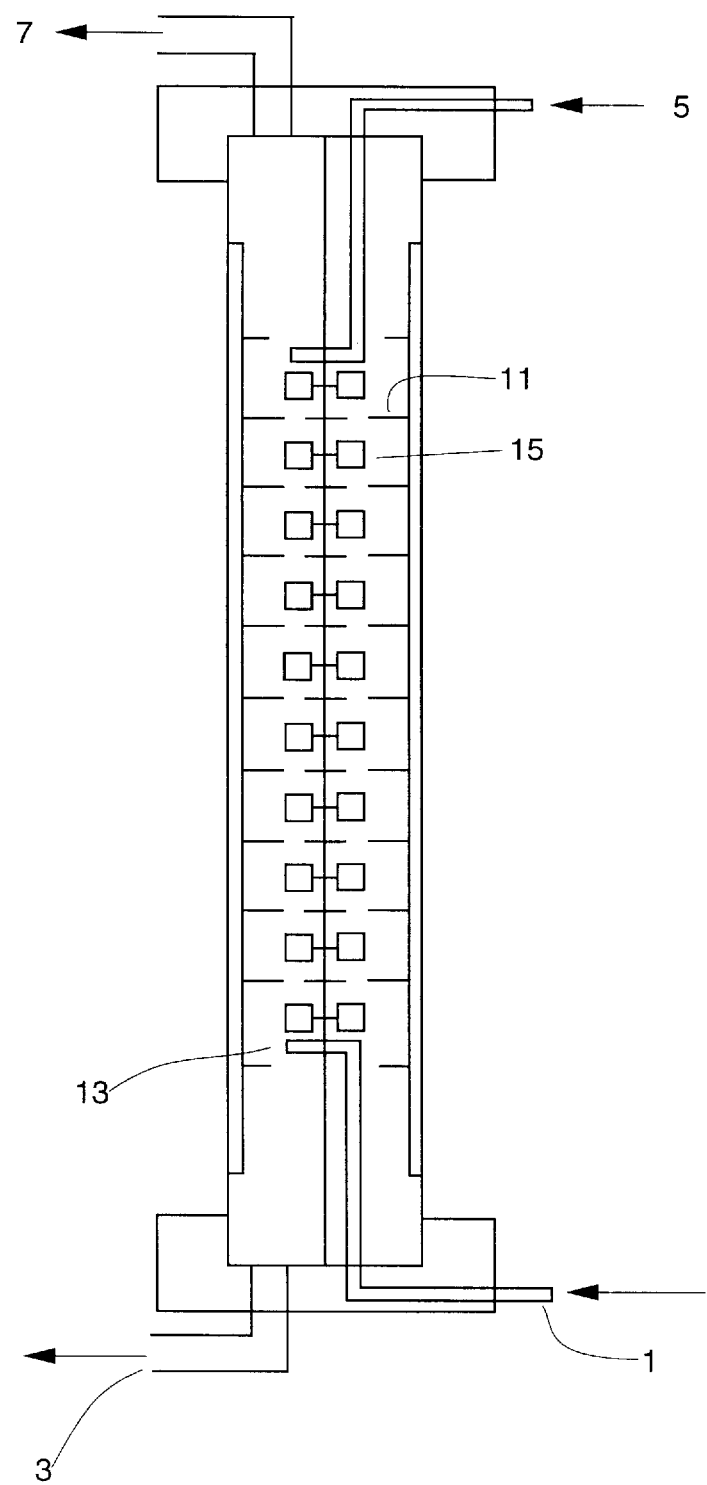

METHOD FOR PURIFYING AN INERT GAS WHILE PREPARING LOWER ALKYL ESTERS

TECHNICAL FIELD

This is a process for purifying an inert gas stream from a transesterification reaction wherein a lower alkyl alcohol is released during the reaction. A second use of the process is to make a lower alkyl, e.g., methyl, esters of fatty acids through a transesterification reaction using gaseous alcohols as a source of the lower alkyl alcohols. The alcohol is diluted with nitrogen or other inert gas carrier and reacted with a fatty acid ester, preferably a triglyceride, to form the corresponding methyl or lower alkyl fatty acid ester.

BACKGROUND OF THE INVENTION

Transesterification reactions are commonly used to make new ester compounds; usually a new alcohol group is added to the acid. Methyl esters are a cheaper carboxylic acid source than acid chlorides or anhydrides, and they are sufficiently reactive to provide a good source of fatty acids for complex esterification reactions. The economics of the reactions are such that the relatively inexpensive cost of methyl esters outweighs any added processing costs. They are primarily used in the preparation of polyol polyesters and other synthetic fats, waxes, diesel fuels and emulsifiers. The lower alkyl alcohol group is chosen because the alcohol can be easily removed in the subsequent transesterification reaction through vacuum distillation or by reducing the partial pressure of the alcohol using a nitrogen or inert gas sparge, driving the transesterification reaction to completion.

Typically, methyl esters of fatty acids are prepared from the naturally occurring fatty acids sources, usually triglycerides from vegetable or animal sources. The methyl alcohol replaces the glycerine. The resultant mixture of methyl esters are easily fractionated, providing a purified source of fatty acids.

This development is a method for making lower alkyl esters of primarily fatty acids by transesterifying a triglyceride with a lower alkyl alcohol using gaseous alcohol in an inert gas carrier. Preferably the reaction is run in a reactive adsorption column, but it can be done in a batch process. The gaseous alcohol mixture is preferably a recovered inert gas sparge from a transesterification process used to make more complex esters, i.e., a polyol polyester synthesis, or emulsifier synthesis reaction. Over 90%, and up to 99.7%, of the methanol is converted into methyl esters, and the triglyceride is converted into glycerine and mono- and di-glycerides. The alcohol free or reduced alcohol nitrogen (inert gas) can then be continuously recycled. This ability to recycle nitrogen improves the economics of these reactions.

Reactive absorption columns have been used for the catalytic esterification of carboxylic acids and for making $C_6$–$C_{22}$ fatty acids triglycerides using alkyl esters. It is believed that the use of these columns for transesterification with a lower alkyl alcohol in an inert gas carrier under the conditions claimed herein is new.

A key economic driver for this process is the integration or close coupling of the methyl ester synthesis and transesterification reactions which use these esters as a fatty acid or carboxylic acid source. Traditionally methanol can be recovered from the inert gas stream by condensation, absorption into organic solvents, (e.g. triethylene glycol) or adsorption onto activated carbon. This reaction when coupled with a polyol polyester synthesis, eliminates a separate methanol recovery system, eliminates handling of methanol and partially reduces the discharge of methanol into the environment.

It is an object of this invention to provide a method for purifying the inert gas stream from a transesterification reaction that uses lower alkyl esters of carboxylic acids as the fatty acid source. It is a further object of this invention to provide a method for making methyl esters for fatty acids through a transesterification reaction using gaseous methanol in a reactive adsorption column.

SUMMARY OF THE INVENTION

A process for preparing lower alkyl esters is claimed which comprises reacting a triglyceride or other fatty acid ester with a gaseous mixture of an inert gas and lower alkyl alcohol at a temperature of between about 20° C. to about 100° C., at a pressure of about 14 psia (pounds per square inch absolute pressure) to about 150 psia in the presence of a catalyst. In the reaction process a purified stream of inert gas is recovered. The alkyl esters are separated from the glycerine by centrifugation or other separation technique and from the mono- and diglycerides by fractionation, as conventionally practiced in the art. The molar ratio of methanol to triglyceride is in the range of about 0.1:1 to about 15:1. The exact molar ratio will depend on what the object of the reaction is, i.e. maximum removal of alcohol from the nitrogen or maximum conversion of the triglyceride to alkyl ester.

DESCRIPTION OF FIGURES

FIG. 1 shows a typical reactive adsorption column and the flow of the materials into the reactor. A variety of column internals can be used. The illustrated column uses interstage baffles (11) with an agitator (15) to control the flow of the triglyceride, and agitation to produce intimate contact of gas and liquid phases.

All percentages herein are by weight unless otherwise indicated.

DETAILED DESCRIPTION OF THE INVENTION

The process is described in detail by referring to methyl esters and methyl alcohol since methyl is the most commonly used lower alkyl group. However, it should be readily understood that any lower alkyl alcohol can be used. By lower alkyl is meant the $C_1$–$C_6$ alkyl groups, including all of their isomers. Monoalcohols are used.

The process is exemplified with triglycerides as the fatty acid source, but any natural or synthetic source of fatty acid esters can be used in the place of the triglyceride. For example, diglycerides, glycol esters, waxes or other sources of fatty acids can be used. Triglyceride is the preferred fatty acid source since it is readily available, a renewable resource, and relatively inexpensive. Marine and fish oils are good sources of polyunsaturated fatty acids; vegetable oils and animal fats and oils are sources of saturated and unsaturated fatty acids. These fats and oils can be fractionated and selectively hydrogenated to produce the desired fatty acids for the formation of the methyl or alkyl esters.

Preferred vegetable oils include corn oil, canola oil, olive oil, cottonseed oil, soybean oil, sunflowerseed oil, high erucic acid rapeseed oil, partially or fully hydrogenated soybean oil, partially or fully hydrogenated canola oil, partially or fully hydrogenated sunflowerseed oil, partially or fully hydrogenated high erucic acid rapeseed oil and partially or fully hydrogenated cottonseed oil.

As used herein, the term "gaseous stream" or "gas stream" is meant to encompass the alcohol and inert gas mixture that is used in the reaction. Nitrogen, carbon dioxide, helium or other inert gas can be used. Nitrogen is preferred due to its ready availability and cost. Steam or water is not acceptable since the water will neutralize the catalyst and can hydrolyze both the triglycerides and the methyl esters that are formed.

Triglyceride is converted into the methyl ester or lower alkyl ester by the following process:

Triglyceride is contacted with a gaseous stream of nitrogen or other inert gas and lower alkyl alcohol in a batch reactor or preferably in a continuous reactive adsorption column. The methanol comprises from 1 to 10% of the gaseous stream. The partial pressure of the alcohol in the gaseous stream affects the solubility of the alcohol and drives the reaction. Therefore, the concentration of the alcohol in the inert gas as well as the temperature and pressure of the entering gas/alcohol stream are important. The gas/methanol stream enters the column at (1) and is dispersed through the sparge ring (13). The flow rate of the gaseous stream, i.e., the nitrogen alcohol mixture, as it enters the column is from about 0.5:1 to about 7.5:1 (weight basis) relative to the triglyceride flow.

The exact shape and structure of the sparge device (13) is not critical to the reaction, and its configuration is easily determined by one skilled in the art. What is important is that the inert gas/alcohol stream be dispersed in the triglyceride in a manner that it contacts the triglyceride effectively allowing the alcohol to be absorbed by and react with the triglyceride, and thus to convert the fatty acids to alcohol esters.

For maximum conversion of triglyceride to alkyl ester, a molar excess of alcohol is used; in the range of 3 moles of alcohol to one mole of triglyceride up to a ratio of about 15:1. This represents a 1 to 5 fold ratio of alcohol to fatty acid group. For maximum removal of methanol from the nitrogen stream, an excess of triglyceride is used. In this case, the alcohol to triglyceride ratio is from 0.1:1 to about 3:1. Under preferred conditions, both high methyl ester conversion and high alcohol removal are achieved.

The triglyceride or other fatty acid ester source is mixed with an esterification catalyst and added to the reactor. In a counter current column reactor, the liquid enters at (5) and flows down the column. The column contains material that disperses nitrogen or inert gas and methanol in the triglyceride. Packing or agitated stages are preferred. Other columns such as tray columns, perforated disk columns, and bubble columns can be used. The exact type of column that is used is not critical and depends on a number of factors which are readily apparent to one skilled in the art.

The nitrogen and methyl alcohol is passed through the triglyceride in a counter current manner and the gas exits at (7). The liquid exits at (3). Cocurrent or batch processing can also be used.

The preferred catalyst is a basic catalyst e.g., an alkali or alkaline earth metal hydroxide, alkoxide or carbonate. Preferably the reaction is catalyzed by the sodium or potassium alkoxide corresponding to the lower alkyl alcohol. When methanol is the lower alkyl alcohol, sodium or potassium methoxide is used. Alkali metal alkoxides are readily available commercially or can be prepared by reaction potassium or sodium with an excess of the alcohol. The most preferred catalysts are sodium or potassium methoxide or potassium carbonate. Acid catalysts such as, ptoluenesulfonic acid, phosphoric acid, potassium or sodium mono- or dihydrogen phosphate, hydrochloric acid or sulfuric acid can also be used. The catalyst is typically used at a level of from about 0.1% to about 1.0% of the triglyceride (weight basis).

As mono- and diglycerides form, they facilitate the reaction and create a foam. The time of the reaction can vary from 5 minutes to 5 hours preferably, from ½ to 2 hours. The exact time depends on the size of the reaction vessel as well as the flow rate of the materials, the temperatures and the pressure.

In a reaction column, refined or refined and bleached vegetable oil is added to the reaction vessel along with the catalyst. Nitrogen and the lower alkyl alcohol are intimately mixed for addition to the vessel. This can be done by either bubbling a stream of nitrogen through the alcohol by vaporizing alcohol into the inert gas or by using a nitrogen stream which is recovered from a transesterification reaction in which the lower alkyl alcohol is generated during the transesterification. A preferred source of this gaseous stream is the transesterification synthesis reaction of polyol polyesters using methyl esters as the fatty acid source. The gaseous stream is mixed with triglyceride in a ratio of about 15 moles of alcohol to each mole of triglyceride to about 3 moles of lower alkyl alcohol per mole triglyceride. This makes the reaction proceed so that the majority (from 80% to 95%) of the triglyceride is converted into methyl esters.

When this reaction is used to cleanse the inert gas stream, the molar ratio of alcohol to triglyceride is from 0.1:1 to about 3:1.

The reaction temperature is between about 20° C. and about 100° C. The pressure is preferably atmospheric or above atmospheric. Generally, the reaction is run at between 14 psia to about 150 psia. The preferred level of pressure is in the range of 14.7 psia to 125 psia, and more preferably 35 to 100 psia.

The esters, glycerine and any monoglycerides or diglycerides are recovered from the bottom of the column as a mixture with any unreacted triglyceride. In the countercurrent column reactor, they exit through (3). The mixture is first separated by settling or by centrifugation wherein the glycerine is also separated from the mixture.

Optionally, additional methanol or alcohol can be added to drive the reaction to completion. In this case, a glycerine separation step is required.

The catalyst and remaining glycerine are removed by water washing of the crude reaction mixture. The catalyst and the glycerine dissolve in the water and the esters are removed by settling or centrifugation. The clean up of the crude reaction mixture is accomplished by conventional processing.

The methyl esters are then separated or purified by distillation or other conventional means. The methyl esters can be further purified by fractionation, including molecular distillation, if desired.

The inert gas used in this reaction is preferably that recovered from a transesterification reaction. In the process herein, the inert gas not only dilutes the methanol stream, but it also provides an inert atmosphere and thus prevents oxidation of the reactants.

The nitrogen exiting this reaction is typically less than 2000 ppm methanol or alcohol and can be as low as 50 ppm alcohol. The lower levels of residual methanol or alcohol in nitrogen are reached with excess triglycerides.

The following examples illustrate this invention, but are not intended to limiting thereof. Examples 1 to 3 are intended to show that you can reach very low levels of residual alcohol in nitrogen (50 ppm to 520 ppm) at a wide range of pressures (15 psig or 85 psig) with stoichiometric excess of triglyceride. Conversion to methyl esters was low in each case ( about 20%).

EXAMPLE 1

| INGREDIENTS | AMOUNT |
|---|---|
| soybean oil | stoichiometric excess (52 lb/hr) |
| sodium methoxide | 0.05 moles/mole oil |
| nitrogen | 32 lb./hr. |
| methanol | 4.0 gm./min. (1.6% of $N_2$) |

In a continuous multi-stage agitated column triglyceride (refined, bleached and deodorized soybean oil) containing sodium methoxide is fed continuously into the top of the reactor. The reactor is 6" in diameter by 48" tall and has 10 agitated stages. The agitator was run at about 1500 rpm. The column was configured as in FIG. 1. The triglyceride is passed countercurrent to a methanol/nitrogen stream fed from the bottom of the reactor. The reactor is held at 38° C., and 64.7 psia (50 psig). The nitrogen/methanol flow is 32 lb./hr. The product nitrogen stream contains 40 ppm methanol. This nitrogen stream is used in the polyol polyester synthesis described in Example 6.

EXAMPLE 2

In a reaction similar to Example 1, a nitrogen gas stream containing 1.6% methanol is passed through the column at 52 lb./hr. Triglyceride containing 0.05 moles solid sodium methoxide per mole triglyceride is fed into the top of the column at 52 lb./hr. The temperature is 43° C. and the pressure is 99.7 psia. The exhaust nitrogen has 80 ppm methanol in it.

EXAMPLE 3

Reactive absorption is carried out in a continuous, counter-current, multi-stage agitated column. Triglyceride is continuously fed into top of reactor and product drawn at bottom. Nitrogen/methanol is fed into bottom of reactor and discharged at top. A stoichiometric excess of triglyceride is used.

Conditions:
Liquid Feed—52 lb./hr. catalyzed triglyceride (0.05 moles solid NaOCH3 per mole triglyceride)
Gas Feed—32 lb./hr. nitrogen, 4.0 grams/min. methanol (1.6% MeOH)
Temperature—98° F. (37° C.)
Pressure—15 psig (29.7 psia)
Results:
520 ppm (0.052%) methanol is present in the exhaust nitrogen.

EXAMPLE 4

Reactive absorption is carried out in a continuous, counter-current, multi-stage agitated column as in the previous examples. Triglyceride is continuously fed into top of reactor and product drawn out the bottom. Nitrogen/methanol is fed into bottom of reactor and discharged at top. Roughly stoichiometric amounts of methanol and triglyceride are used.

Conditions:
Liquid Feed—80 lb./hr. catalyzed triglyceride (0.15 moles solid NaOCH3 per mole triglyceride)

Gas Feed—200 lb./hr. nitrogen, 7.8 lb./hr. methanol
Temperature—130° F. (54° C.)
Pressure—65 psig (79.7 psia)
Results:
2000 ppm (0.20%) methanol in exhaust nitrogen
81% conversion of triglyceride to methyl esters

EXAMPLE 5

A reactive absorption conversion of triglyceride to methyl esters is carried out in a 1.5 liter batch agitated reactor. A stoichiometric excess of methanol is bubbled through catalyzed triglyceride.

Conditions:
Liquid—883 grams of triglyceride, 3.05 grams of sodium methoxide catalyst
Gas—1.6 liters/min. nitrogen, 2.1 grams/min. methanol
Temperature—194° F. (90° C.)
Pressure—atmospheric (14.7 psia)
Results:
55% conversion of triglyceride to methyl esters in 30 minutes.
80% conversion to methyl esters in 75 minutes.

Reaction mixture at 80% conversion was allowed to stand resulting in a two phase system. The heavier phase (primarily glycerine) was removed. The remaining mixture was further reacted under conditions similar to those described above for 75 minutes, leading to 96% methyl esters in the final product.

What is claimed is:

1. A continuous process for purifying an inert gas stream containing a lower alkyl alcohol comprising:

(1) intimately mixing an inert gas containing a lower alkyl alcohol with a fatty source at a temperature of between about 20° C. to about 100° C., at a pressure of from about 14 to about 150 psia in the presence of a catalyst; and (2) recovering the methyl esters and the purified inert gas stream.

2. A process according to claim 1 wherein the reaction is conducted at a pressure of from between about 35 and about 100 psia.

3. A process according to claim 2 wherein the catalyst is selected from the group consisting of sodium methoxide, sodium or potassium alkoxide, sodium or potassium carbonate, and mixtures thereof.

4. A process according to claim 1 wherein the inert gas is nitrogen.

5. A process according to claim 1 wherein the lower alkyl alcohol is methanol and the inert gas is nitrogen.

6. A process according to claim 1 wherein the fatty acid source is a triglyceride selected from the group consisting of vegetable oils, hydrogenated vegetable oils, marine oils, and animal fats and oils.

7. A process according to claim 6 wherein the triglyceride is selected from the group consisting of canola oil, olive oil, cottonseed oil, soybean oil, sunflowerseed oil, high erucic acid rapeseed oil, partially or fully hydrogenated soybean oil, partially or fully hydrogenated canola oil, partially or fully hydrogenated sunflowerseed oil, partially or fully hydrogenated high erucic acid rapeseed oil, partially or fully hydrogenated cottonseed oil and mixtures thereof.

8. A process according to claim 6 wherein the molar ratio of lower alkyl alcohol to triglyceride is about 0.1:1 to about 15:1.

9. A process according to claim 8 wherein the reaction is conducted in a reaction column and the molar ratio of lower alkyl alcohol to triglyceride is about 0.1:1 to about 3:1.

10. A continuous process for purifying an inert gas stream containing a lower alcohol comprising:
   (1) intimately mixing an inert gas containing a lower alkyl alcohol with a fatty acid source at a temperature of between about 20° C. and to about 100° C. at a pressure of from about 14 to 150 psia in the presence of a catalyst wherein the reaction is carried out in a column selected from a group consisting of packed columns, tray columns, perforated disk columns, bubble columns and agitated columns; and
   (2) recovering the methyl esters and the purified inert gas stream.

11. A continuous process for purifying an inert gas stream containing a lower alkyl alcohol comprising the steps of:
   (1) intimately mixing an inert gas containing a lower alkyl alcohol with a fatty acid source;
   (2) reacting the fatty acid source with the lower alkyl alcohol at a temperature of between about 20° C. to about 100° C., at a pressure of from about 14 to 150 psia, and in the presence of a catalyst, to form a lower alkyl ester;
   (3) recovering the lower alkyl ester; and
   (4) recovering the purified inert gas stream.

12. A process according to claim 11 wherein the reacting step is conducted at a pressure of from about 35 psia to about 100 psia.

13. A process according to claim 12 wherein the catalyst is selected from the group consisting of sodium methoxide, sodium alkoxide, potassium alkoxide, sodium carbonate, potassium carbonate, and mixtures thereof.

14. A process according to claim 11 wherein the inert gas is nitrogen.

15. A process according to claim 11 wherein the lower alkyl alcohol is methanol and the inert gas is nitrogen.

16. A process according to claim 11 wherein the fatty acid source is a triglyceride selected from the group consisting of vegetable oils, hydrogenated vegetable oils, marine oils, and animal fats and oils.

17. A process according to claim 16 wherein the triglyceride is selected from the group consisting of canola oil, olive oil, cottonseed oil, soybean oil, sunflowerseed oil, high erucic acid rapeseed oil, partially or fully hydrogenated soybean oil, partially or fully hydrogenated canola oil, partially or fully hydrogenated sunflowerseed oil, partially or fully hydrogenated high erucic acid rapeseed oil, partially or fully hydrogenated cottonseed oil, and mixtures thereof.

18. A process according to claim 16 wherein the intimate admixture contains a molar ratio of the lower alkyl alcohol to the triglyceride of from about 0.1:1 to about 15:1.

19. A process according to claim 18 wherein the reacting step is conducted in a reaction column and the molar ratio of the lower alkyl alcohol to the triglyceride is about 0.1:1 to about 3:1.

20. A process according to claim 19 wherein the reaction column is selected from a group consisting of packed columns, tray columns, perforated disk columns, bubble columns and agitated columns.

21. A process according to claim 11 wherein in step (1) the intimate mixture contains from 1% to 10% by weight the lower alkyl alcohol.

22. A continuous process for preparing lower all esters comprising the steps of:
   (1) reacting a fatty acid source with an intimate mixture of an inert gas and a lower alkyl alcohol at a temperature of from about 20° C. to about 100° C., at a pressure of from about 14 psia to about 150 psia and in the presence of a catalyst to form a lower alkyl ester; and
   (2) recovering the lower alkyl ester.

23. A process according to claim 22 wherein the reacting step is conducted at a pressure of from about 35 psia and about 100 psia.

24. A process according to claim 23 wherein the catalyst is selected from the group consisting of sodium methoxide, sodium or potassium alkoxide, sodium or potassium carbonate, and mixtures thereof.

25. A process according to claim 22 wherein the inert gas is nitrogen.

26. A process according to claim 22 wherein the lower alkyl alcohol is methanol and the inert gas is nitrogen.

27. A process according to claim 22 wherein the fatty acid source is a triglyceride selected from the group consisting of vegetable oils, hydrogenated vegetable oils, marine oils, and animal fats and oils.

28. A process according to claim 27 wherein the triglyceride is selected from the group consisting of canola oil, olive oil, cottonseed oil, soybean oil, sunflowerseed oil, high erucic acid rapeseed oil, partially or fully hydrogenated soybean oil, partially or fully hydrogenated canola oil, partially or fully hydrogenated sunflowerseed oil, partially or fully hydrogenated high erucic acid rapeseed oil, and mixtures thereof.

29. A process according to claim 27 wherein in step (1) a molar ratio of the lower alkyl alcohol to the triglyceride is from about 0.1:1 to about 15:1.

30. A process according to claim 22 wherein the reacting step (1) occurs in a reaction column.

31. A process according to claim 30 wherein the column reaction is selected from the group consisting of packed columns, tray columns, perforated disk columns, bubble columns and agitated columns.

* * * * *

UNITED STATES PATENT AND TRADEMARK OFFICE
CERTIFICATE OF CORRECTION

PATENT NO. : 5,844,111
DATED : December 1, 1998
INVENTOR(S) : Eric Paul Granberg et al.

It is certified that error appears in the above-indentified patent and that said Letters Patent is hereby corrected as shown below:

Cover page, under item [56] Attorney, Agent, or Firm, "Nesbit;" should read -- Nesbitt; --.

Column 8, line 12, "all" should read -- alkyl --.

Column 8, line 17, after "150 psia" insert -- , --.

Column 8, line 18, after "catalyst" insert -- , --.

Signed and Sealed this

Twenty-seventh Day of March, 2001

Attest:

NICHOLAS P. GODICI

*Attesting Officer*  *Acting Director of the United States Patent and Trademark Office*